(12) United States Patent
Lovas et al.

(10) Patent No.: US 11,633,406 B2
(45) Date of Patent: Apr. 25, 2023

(54) INDUSTRIAL PROCESS FOR THE PREPARATION OF HIGH PURITY ESTETROL

(71) Applicant: RICHTER GEDEON NYRT., Budapest (HU)

(72) Inventors: Róbert Lovas, Budapest (HU); Sándor Mahó, Budapest (HU); Ildikó Bacsa, Szeged (HU); Beatrix Mayer, Pilis (HU)

(73) Assignee: RICHTER GEDEON NYRT., Budapest (HU)

( * ) Notice: Subject to any disclaimer, the term of this patent is extended or adjusted under 35 U.S.C. 154(b) by 0 days.

(21) Appl. No.: 17/639,206

(22) PCT Filed: Sep. 2, 2020

(86) PCT No.: PCT/IB2020/058148
§ 371 (c)(1),
(2) Date: Feb. 28, 2022

(87) PCT Pub. No.: WO2021/044302
PCT Pub. Date: Mar. 11, 2021

(65) Prior Publication Data
US 2022/0296609 A1 Sep. 22, 2022

(30) Foreign Application Priority Data
Sep. 3, 2019 (HU) .................................. 1900315

(51) Int. Cl.
*A61K 31/566* (2006.01)
*A61K 31/585* (2006.01)
*C07J 1/00* (2006.01)

(52) U.S. Cl.
CPC .......... *A61K 31/566* (2013.01); *A61K 31/585* (2013.01); *C07J 1/007* (2013.01)

(58) Field of Classification Search
CPC ...... A61K 31/566; A61K 31/585; C07J 1/007
See application file for complete search history.

(56) References Cited

FOREIGN PATENT DOCUMENTS

| WO | WO-2002094275 A1 | 11/2002 |
|---|---|---|
| WO | WO-2002094276 A1 | 11/2002 |
| WO | WO-2002094278 A1 | 11/2002 |
| WO | WO-2002094279 A1 | 11/2002 |
| WO | WO-2003041718 A1 | 5/2003 |
| WO | WO-2003103684 A1 | 12/2003 |
| WO | WO-2003103685 A1 | 12/2003 |
| WO | WO-2004006936 A1 | 1/2004 |
| WO | WO-2004037269 A1 | 5/2004 |
| WO | WO-2004041839 A2 | 5/2004 |
| WO | WO-2007081206 A1 | 7/2007 |
| WO | WO-2008085038 A2 | 7/2008 |
| WO | WO-2013012328 A1 | 1/2013 |
| WO | WO-2013021025 A1 | 2/2013 |
| WO | WO-2013034780 A2 | 3/2013 |
| WO | WO-2013050553 A1 | 4/2013 |
| WO | WO-2013156329 A1 | 10/2013 |
| WO | WO-2015040051 A1 | 3/2015 |
| WO | WO-2016203006 A1 | 12/2016 |
| WO | WO-2016203009 A1 | 12/2016 |
| WO | WO-2016203044 A1 | 12/2016 |
| WO | WO-2018024912 A1 | 2/2018 |
| WO | WO-2018065076 A1 | 4/2018 |
| WO | WO-2019025031 A1 | 2/2019 |
| WO | WO-2019154899 A1 | 8/2019 |
| WO | WO-2021058716 A1 | 4/2021 |

OTHER PUBLICATIONS

Adis Insight, "Estetrol—Mithra Pharmaceuticals/Pantarhei Bioscience," Drug profile, accessed at https://adisinsight.springer.eom/drugs/800044874, last updated Jun. 24, 2021.

Apter, D., et al., "Estretrol combined with drospirenone: an oral contraceptive with high acceptability, user satisfaction, well-being and favourable body weight control," *European Journal of Contraception & Reproductive Health Care* 22(4):260-267, Taylor & Francis, England (Aug. 2017).

Coelingh Bennink, H.J.T., et al., "Estetrol review: profile and potential clinical applications," *Climacteric* 11 Suppl 1:47-58, Taylor & Francis, England (2008).

Fishman, J., et al., "Synthesis of epimeric 15-hydroxy estriols, new and potential metabolites of estradiol," *Journal of Organic Chemistry* 33(8):3133-3135, American Chemical Society, United States (Aug. 1968).

Fishman, J., et al., "Synthesis of estra-1,3,5(10)-trien-3, 15α, 16α, 17β-tetrol. A new metabolite of estradiol.," *Tetrahedron Letters* 8(30):2929-2932, Elsevier, Netherlands (1967).

(Continued)

*Primary Examiner* — San Ming R Hui
(74) *Attorney, Agent, or Firm* — Sterne, Kessler, Goldstein & Fox P.L.L.C.

(57) ABSTRACT

The invention relates to the preparation of estetrol of formula (I), derivatives thereof protected at positions 3,15α, 16α,17β of general formula (III), and 3-hydroxy derivatives thereof protected at positions 15α,16α,17β of general formula (IV), and to the intermediates of general formulae (III) and (IV) applied in the process. Another aspect of the invention is the use of estetrol of formula (I) obtained by the process of the invention for the preparation of a pharmaceutical composition.

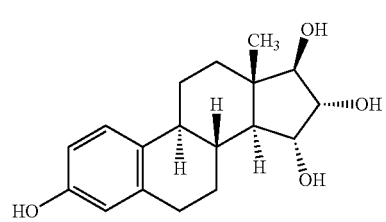

I

16 Claims, No Drawings

(56) References Cited

OTHER PUBLICATIONS

Gaspard, U., et al., "Estetrol (E4), the next generation hormone therapy (HT) for menopausal symptoms: phase 2b clinical trial results," *Maturitas 124*:153, Abstract P09, Elsevier, Netherlands (Jun. 2019).
International Search Report and Written Opinion for International Application No. PCT/IB2020/058148, European Patent Office, Netherlands, dated Nov. 12, 2020, 11 pages.
Nambara, T., et al., "Syntheses of estetrol monoglucuronides," *Steroids 27*(1): 111-122, Elsevier, Netherlands (Jan. 1976).
Suzuki, E., et al., "Synthesis of 15α-hydroxyestrogen 15-N-acetylglucosaminides," *Steroids 60*:211-284, Elsevier, Netherlands (Mar. 1995).
Tskitishvili, E., et al., "Estrogen receptors and estetrol—dependent neuroprotective actions: a pilot study," *Journal of Endocrinology 232*(1):85-95, Bioscientifica, United Kingdom (2017).

INDUSTRIAL PROCESS FOR THE PREPARATION OF HIGH PURITY ESTETROL

THE FIELD OF THE INVENTION

The invention relates to the preparation of estetrol (estra-1,3,5(10)-triene-3,15α,16α,17β-tetrol) of formula (I), derivatives thereof protected at positions 3,15α,16α,17β of general formula (III), and 3-hydroxy derivatives thereof protected at positions 15α,16α,17β of general formula (IV), and to the intermediates of general formulae (III) and (IV) applied in the process. Another aspect of the invention is the use of estetrol of formula (I) obtained by the process of the invention for the preparation of a pharmaceutical composition.

THE BACKGROUND OF THE INVENTION

Estetrol (estra-1,3,5(10)-triene-3,15α,16α,17β-tetrol) of formula (I) is a compound having weak estrogenic activity produced endogenously by the fetal liver during human pregnancy.

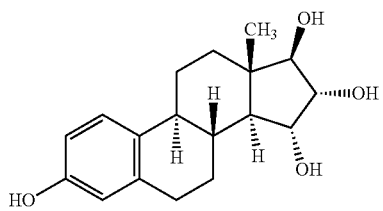

I

Estetrol was found to be efficacious in hormone replacement therapy, a method of treating vaginal dryness, a method of treating perimenopausal symptoms (for example hot flashes, night sweats), a method of contraception, a method of enhancing libido, a method of treating skin and promoting wound healing, a method of treating or preventing an autoimmune disorder, breast tumors, prostate cancer and colorectal tumors, and a method of neuroprotection (for example neonatal encephalophaty) (WO 02/094275 A1, WO 02/094276 A1, WO 02/094278 A1, WO 02/094279 A1, WO 03/041718 A1, WO 03/103684 A1, WO 03/103685 A1, WO 2004/006936 A1, WO 2004/037269 A1, WO 2007/081206 A1, WO 2008/085038 A2, WO 2013/021025 A1, WO 2013/156329 A1, WO 2018/024912 A1, WO 2018/065076 A1, WO 2019/025031 A1; Estetrol last updated on 14 May 2019—https://adisinsight.springer.com/drugs/800044874; Gaspard et al., Maturitas 124 (2019) p. 153 Abstract P09; Apter et al. Eur J Contracept Reprod HC (2017) 22(4):260-267; Tskitishvili et al., J Endocrinol. (2017) 232(1):85-95; Coelingh Bennick et al., Climacteric (2008) 11(Suppl1):47-58).

The synthesis of estetrol depicted in Reaction Scheme 1 was for the first time described by Fishman et al. (Fishman, J and Guzik, H., *Tetrahedron Letters*, 1967, 30:2929-2932). Reduction of the starting 15-ene-17-keto compound with lithium tetrahydroaluminate gave an allyl alcohol type compound from which diacetate was formed. Oxidation of the diacetate with osmium-tetroxide in pyridine gave estetrol diacetate, which was boiled in methanol with potassium acetate to give estetrol. The publication does not include yield and purity data, melting point (230-235° C.), specific rotation ($[\alpha]_D^{26}=135°$ (EtOH)) and NMR (60 MHz) data were provided as proof of identity data.

Reaction Scheme 1

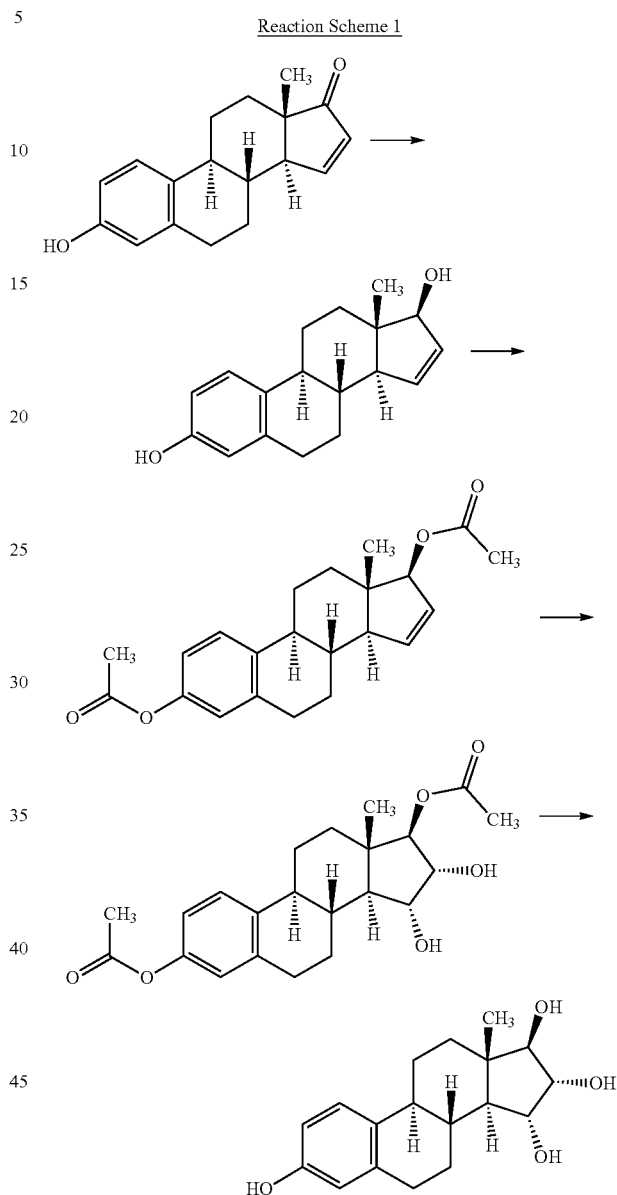

In the synthesis described by Suzuki et al. (Suzuki, E., Namba, S., Kuruhara, H., Goto, J., Matsuki, Y., Nambara, T., Steroids, 1995, 60, 277-284) depicted in Reaction Scheme 2 a 15-ene-17-acetoxy compound was oxidized in benzene with an equivalent of osmium tetroxide in the presence of pyridine. The resulting diacetate isomers were separated by column chromatography, to give 15α,16α,17β-diacetate in 46% yield and the 15β,16β,17β-diacetate isomer in 12% yield.

Isomer ratio calculated from the given quantities of the obtained products is 78.9/21.1 (15α,16α/15β,16β).

The alkaline hydrolysis of 15α,16α,17β-diacetate gave estetrol in 67% yield. Purity data were not provided, 233-235° C. was given as the melting point of the product.

Reaction Scheme 2

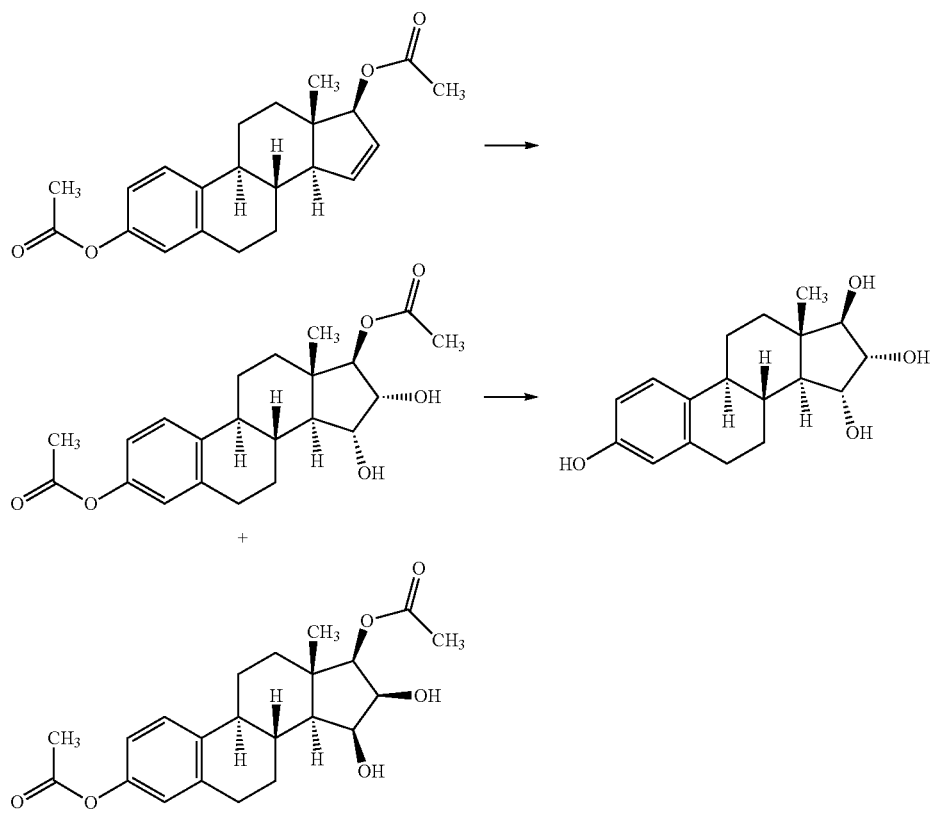

In the patent application WO 2004/041839 A2 (Pantarhei)—Reaction Scheme 3—starting from estrone protected as 3-benzyl ether the $\Delta^{15}$-estradiol-benzyl ether 17-acetate is formed by several known steps that is oxidized with polymer-bound osmium tetroxide by treatment with a heptane-ethyl acetate solvent mixture to give a crude product which is then crystallized in a ternary solvent mixture (heptane-ethyl acetate-ethanol) to give estetrol-benzyl ether-17-acetate in 43% yield with a purity of 98.7% (isomeric purity: 99.5%). Deprotection by catalytic hydrogenation (92% yield) and alkaline hydrolysis (92.5% yield) afforded the estetrol compound. Data on the purity of the product is given as 99.5%. The same solution is disclosed in the patent application WO 2013/012328 A1 (Donesta) as well.

According to the description a pure intermediate is given at a high loss while crystallization is carried out from a technologically disadvantageous ternary solvent mixture. This solution also raises an economic question.

Reaction Scheme 3

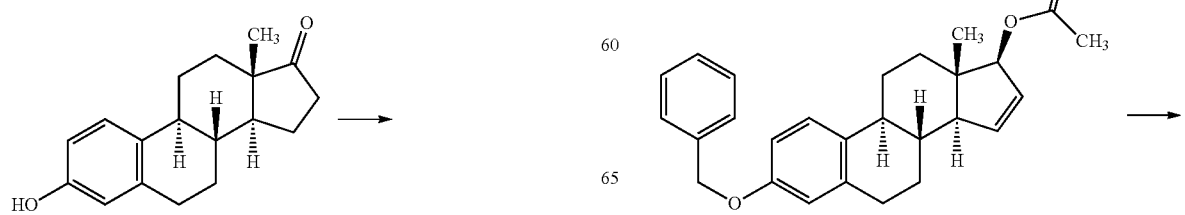

-continued

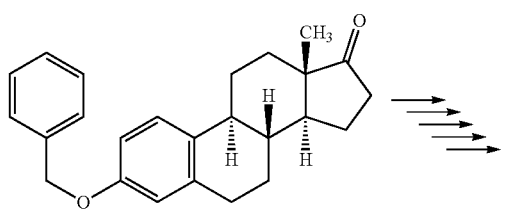

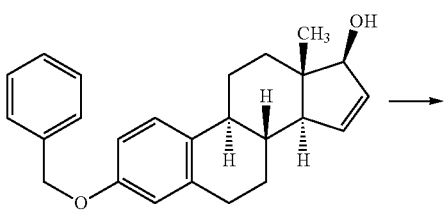

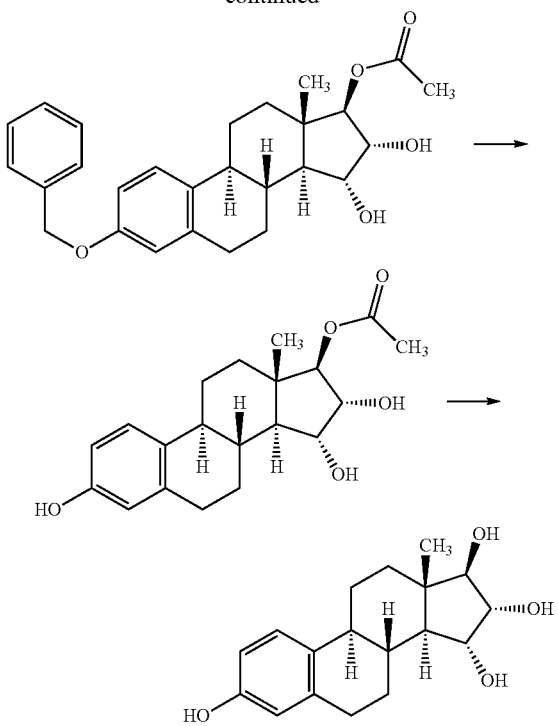

The patent application WO2013/050553 A1 (Estetra)—Reaction Scheme 4—also describes potassium permanganate as an oxidizing agent, but does not give isomer ratio, purity and yield data.

Reaction Scheme 4

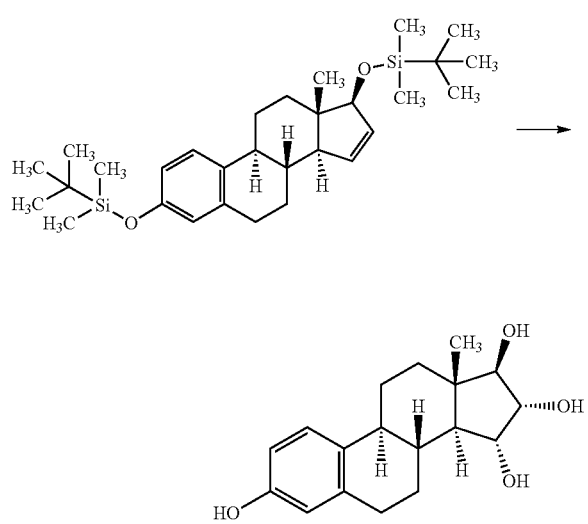

In the examples of patent application WO 2013/034780 A2 (Crystal Pharma)—Reaction Scheme 5—osmium tetroxide bound to poly(4-vinylpyridine) (PVP) is used as oxidizing agent for the cis-hydroxylation at 55-60° C. temperature. In the case of osmium tetroxide oxidation of the $\Delta^{15}$-17-acetoxy derivative 15α,16α/15β,16β isomeric ratio of 80/20 was measured in the reaction mixture, the product was obtained in 88% yield, but no purity data are given.

Reaction Scheme 5

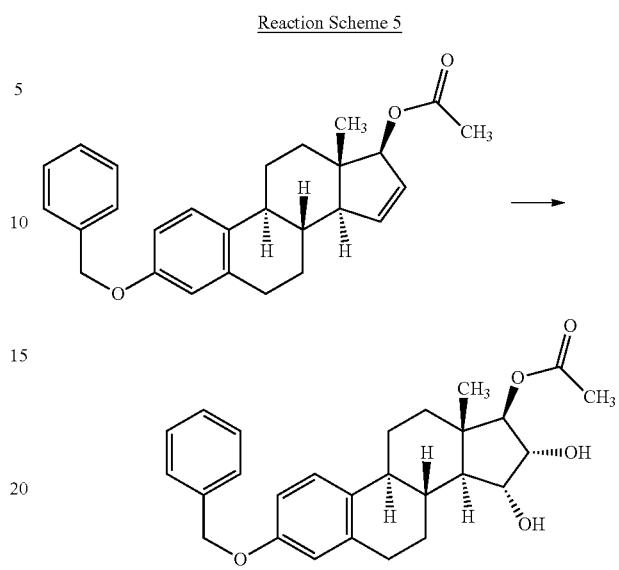

In the case of the $\Delta^{15}$-17β-hydroxy compound, a 62% yield and 15α,16α/15β,16β isomeric ratio of 90/10 was provided but no purity data reported:

Reaction Scheme 6

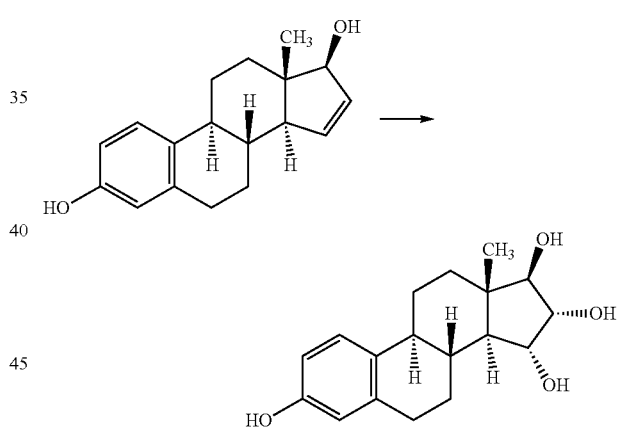

In the case of the benzyl ether, a 15α,16α/15α,16α isomeric mixture with a ratio of 90/10 is obtained in 99% yield, but no purity data are given:

Reaction Scheme 7

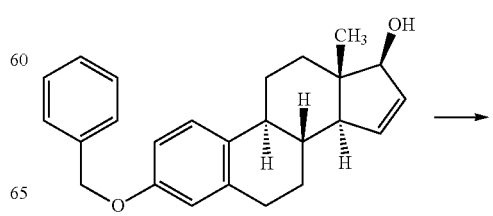

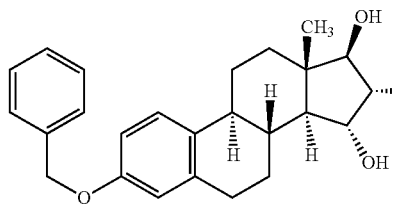

In the case of the 3-benzoyl compound a 15α,16α/15α,16a isomeric mixture with a ratio of 90/10 is obtained in 92% yield, but no purity data are given:

Reaction Scheme 8

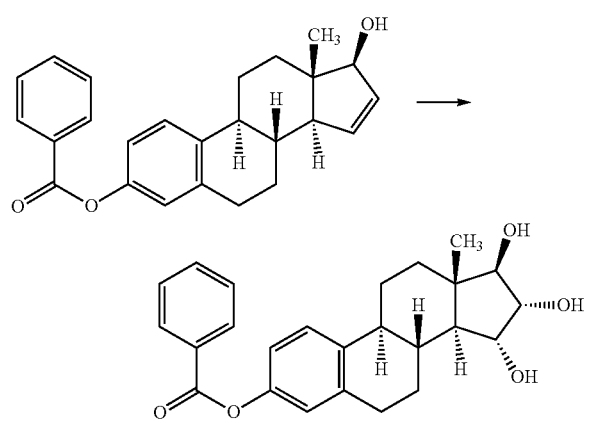

In the case of t-butyl-dimethyl-silyl ether compound a 15α,16α/15β,16β isomeric mixture with a ratio of 90/10 is obtained in 101% yield, but no purity data are given:

Reaction Scheme 9

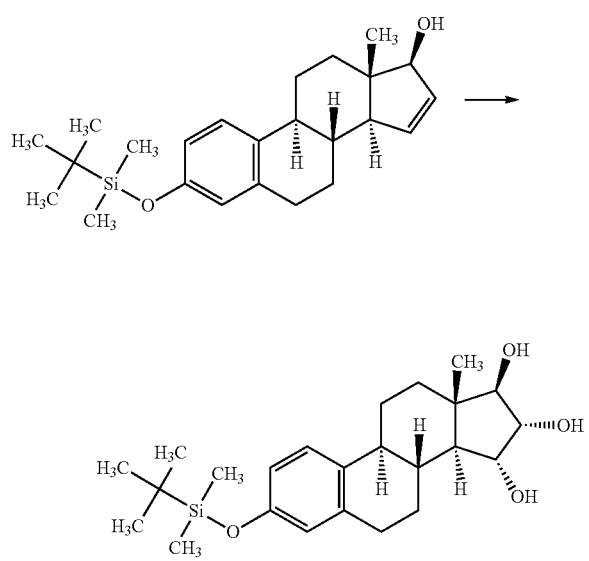

In the case of (1-butoxyethyl)-ether compound a 15α,16α/15β,16β isomeric mixture with a ratio of 90/10 is obtained in 96.5% yield, but no purity data are given:

Reaction Scheme 10

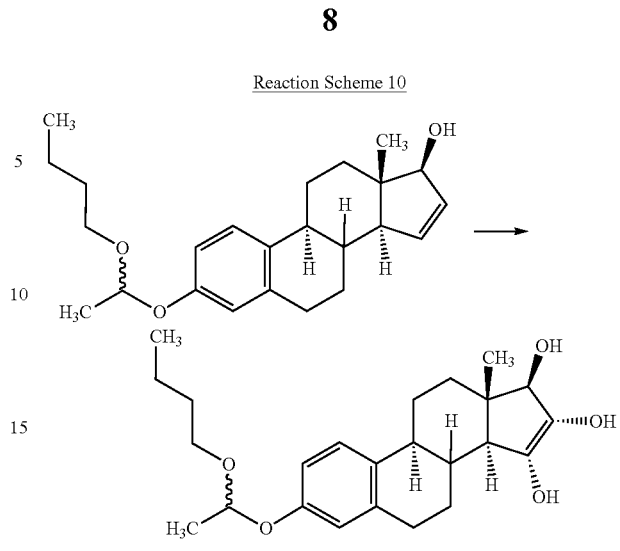

WO 2013/034780 A2 (Crystal Pharma) does not provide information on the purity of the 3-OH protected estetrol derivatives of formula (I) disclosed therein, does not disclose the preparation of estetrol therefrom, and its teaching does not allow the preparation of estetrol in active substance purity to be realized.

The patent application WO 2015/040051 A1 (Crystal Pharma) demonstrates the cis-hydroxylation through derivatives of $\Delta^{15}$-3,17β-dihydroxy having identical or differing protecting groups. Extremely low (1-9%) conversion with potassium permanganate oxidising agents is described. Using osmium tetroxide-PVP oxidising agent, estetrol derivatives protected on hydroxyl groups at positions 3 and 17 are obtained with good conversion. Deprotection individually yields estetrol as a 15α,16α/15β,16β isomeric mixture with a ratio of 98/2-99/1. Purity data are not given in the description. In addition, the description does not contain any information on how to prepare estetrol in active substance purity from the obtained intermediates.

From all this, it can be concluded that either the method of preparation of the estetrol in drug grade purity is not solved, or the production of the pure active substance can be solved with unfavorable yield and low economicalness.

State-of-the-art pharmacopoeial requirements now prescribe a number of test methods, such as high-performance liquid chromatographic purity test methods, as well as dictate and limit the number and amount of contaminants. In the case of steroidal active substances, the general requirement is to apply a limit of 0.5% total impurities and an individual impurity limit of 0.10%. In order to meet the requirements with the quality of the target product, it is expedient to prepare the key intermediate(s) in the appropriate purity, which is especially true for a compound with unfavorable crystallization and purification properties, such as e.g. estetrol.

In view of the above, an unmet need still persist to provide an alternative industrial process for the production of estetrol that allows its production in high purity and can be carried out via intermediates with advantageous properties (e.g. crystallization, purification, isolability, yield).

THE SUMMARY OF THE INVENTION

The invention relates to the process of preparation of estetrol of formula (I), derivatives thereof protected at positions 3,15α,16α,17β of general formula (III), and 3-hydroxy derivatives thereof protected at positions 15α,16α, 17β of general formula (IV), and to the intermediates of general formulae (III) and (IV) applied in the process.

The industrial process of the invention is the preparation of estetrol of formula (I) starting from the compound of formula (II).

The triol derivatives protected at position 3 of formula (II) can be prepared according to the method described in patent application WO 2013/034780 A2 (Crystal Pharma)—Reaction Scheme 7—starting from 3-benzyloxy-estra-1,3,5(10), 15-tetraene-17-ol.

The compounds of general formula (III) are obtained by acylation of the compound of formula (II) and their purification.

The compounds of general formula (IV) are obtained by debenzylation of compounds of general formula (III).

The estetrol of formula (I) is prepared by the basic hydrolysis of compounds of general formula (IV).

The invention also relates to intermediates of general formulae (III) and (IV) of the process described above.

The invention further relates to the use of estetrol of formula (I) obtained by the process described by the invention for the preparation of a pharmaceutical composition.

THE DETAILED DESCRIPTION OF THE INVENTION

The invention relates to the process of preparation of estetrol of formula (I), derivatives thereof protected at positions 3,15α,16α,17β of general formula (III), and 3-hydroxy derivatives thereof protected at positions 15α,16α, 17β of general formula (IV), and to the intermediates of general formulae (III) and (IV) applied in the process.

The industrial process of the invention is the preparation of estetrol of formula (I) starting from the compound of formula (II) according to the following reaction scheme, wherein R denotes methyl-group or hydrogen:

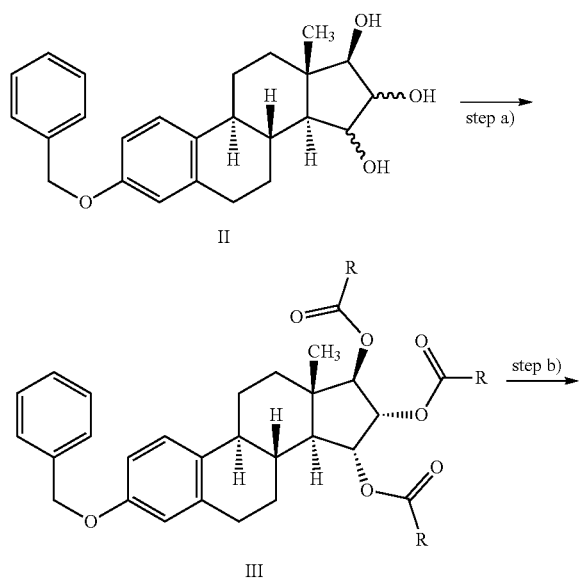

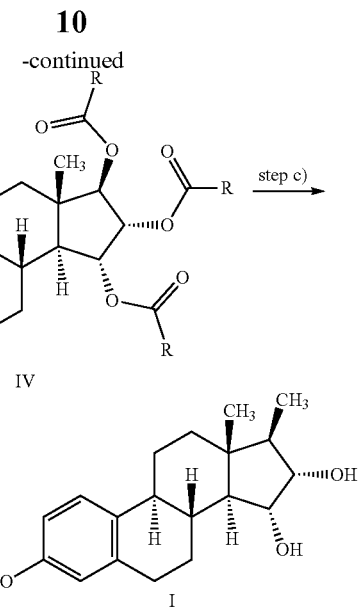

The triol derivatives protected at position 3 of formula (II) can be prepared according to the method described in patent application WO 2013/034780 A2 (Crystal Pharma) i.e. the exemplified compound 7 disclosed therein, the 3-benzyloxy-estra-1,3,5(10),15-tetraene-17-ol is oxidized with an oxidizing agent such as potassium osmate or osmium-tetroxide, optionally in the presence of a co-oxidant such as trialkylamine N-oxide, such as trimethyl- or triethyl-amine N-oxide, in a water-miscible solvent such as 2-butanone, acetone, tetrahydrofuran, tert-butanol, preferably in 2-butanone.

Step (a) Acylation of 15,16,17-Triol Derivative

In step a) of the process according to the invention the estetrol derivative protected at positions 3,15α,16α,17β represented by general formula (III) is obtained by, with or without isolation, the acylation of the 15,16,17-triol derivative protected at position 3 of formula (II) in a suitable solvent, using a suitable reactant.

The solvent used in the acylation is a solvent selected from the group consisting of aliphatic and aromatic hydrocarbons, halogenated hydrocarbons, esters, and ethers, preferably water-immiscible solvents, such as toluene, dichloromethane or ethyl acetate.

In one embodiment, the reactant used for the acylation when is R=methyl (acetylation), is preferably acetic anhydride, acetyl chloride, or -bromide.

In another embodiment, the reactant used for the acylation when is R=hydrogen (formylation), is preferably acetic acid-formic acid mixed anhydride.

The acylation is carried out in the presence of an amine base, preferably pyridine or 4-dimethylaminopyridine.

The acylation is carried out under an inert atmosphere, preferably under $N_2$ atmosphere.

In one embodiment, the acylation step further comprises crystallizing the resulting compound of formula (III) from $C_{1-3}$ alcohols, preferably methanol.

In another embodiment, step (a) can be performed sequentially to the above-mentioned dihydroxylation followed by acylation without purification and/or isolation of the intermediates—the compounds of formula (II)—while still obtaining a high purity end product in good yield. This is particularly advantageous in industrial applications, where reducing the number of process steps results in both an economic advantage and a simplification of the process, as steps such as purification and/or isolation between the two steps will no longer be necessary.

The present invention provides a compound of general formula (III) wherein R is methyl or hydrogen, i.e. (15α,16α,17β)-3-(benzyloxy)estra-1,3,5(10)-triene-15,16,17-triyl triacetate (Example 1) and (15α,16α,17β)-3-(benzyloxy)estra-1,3,5(10)-triene-15,16,17-triyl triformiate (Example 3).

Step (b) Debenzylation of 3,15,16,17-Protected Derivative

In step b) of the process according to the invention the 3-hydroxy estetrol derivative protected at positions 15α, 16α,17β of general formula (IV) is obtained by removing the benzyl protecting group at position 3 of the derivative represented by the general formula (III) by transfer or catalytic hydrogenation.

In one embodiment, the debenzylation is performed by catalytic hydrogenation with hydrogen gas, wherein the catalyst is selected from the group consisting of palladium or palladium on a support (carbon, aluminium-oxide, etc.). The catalyst is preferably Pd/C. The solvent used for the catalytic hydrogenation is selected from the group consisting of alcohols, esters and ketones, preferably ethyl acetate.

In another embodiment, the debesylation is performed by transfer hydrogenation using cyclohexene reagent. The solvent used for the transfer hydrogenation is an alcohol, preferably ethanol.

The debenzylation step further comprises crystallizing the resulting compound of general formula (IV) from esters, hydrocarbons, alcohols, or mixtures thereof, preferably from a mixture of ethyl acetate/n-heptane.

The present invention provides a compound of general formula (IV) wherein R is hydrogen, i.e. (15α,16α,17β)-3-hydroxyestra-1,3,5(10)-triene-15,16,17-triyl triformiate (Example 4).

Step (c) Hydrolysis of 15,16,17-Acyl Protected Derivative

In step c) of the process according to the invention the estetrol of the formula (I) is prepared by deprotecting the derivative of general formula (IV) in an alkaline medium with an alkali carbonate or alkali hydroxides in a suitable solvent.

The solvent used in the hydrolysis is selected from the group consisting of water, an alcohol-type solvent, or a mixture thereof, preferably $C_{1-3}$ alcohols, more preferably a mixture of methanol and water.

In one embodiment, the hydrolysis is carried out in the presence of an alkali carbonate or an alkali hydrogencarbonate, preferably potassium carbonate.

In another embodiment, the hydrolysis is carried out in the presence of an alkali alcoholate or an alkali hydroxide, preferably sodium or lithium hydroxide.

Based on the above, the person skilled in the art can easily select reagents, solvents, temperatures, pressures and other reaction condition. The starting materials, reagents and solvents used in the process of the invention are commercially available and/or can be easily prepared by a person skilled in the art. The purity of the products disclosed in the examples was determined by high performance liquid chromatographic separation techniques known to those skilled in the art, using the most widely used silica gels (e.g. Ascentis, Kintex) as the stationary phase and a multicomponent mixture of the commonly used eluents (e.g. water, methanol, acetonitrile) with a linear gradient set.

While the compound of formula (I) and the 15α,16α,17β-triols protected at position 3 of formula (II) described in the literature have unfavorable crystallization properties, unexpectedly the compounds of general formulae (III) and (IV) crystallize well, can be purified in high yields and can be separated from the isomeric by-product with high selectivity.

In terms of carrying out the invention, steps (a) to (c) are more preferred when R denotes methyl group.

Another embodiment of the invention is the use of estetrol of formula (I) obtained by the process described above for the preparation of a pharmaceutical composition.

The term "pharmaceutical composition" (or "composition") refers to a mixture or solution comprising an active ingredient, such as a compound of formula (I), to be administered to a patient, such as a human in need thereof, preferably a premenopausal or postmenopausal woman, in a therapeutically effective amount together with pharmaceutically acceptable excipients (WO 2016/203006 A1, WO 2016/203009 A1, WO 2016/203044 A1).

The pharmaceutical compositions of the present invention may be formulated in a variety of dosage forms, such as solid or liquid dosage forms. Preferably, the pharmaceutical composition is a solid oral dosage form, such as tablets (e.g. buccal, sublingual, effervescent, chewable, orodispersible).

The compound of formula (I) of the present invention may be co-administered with pharmaceutically acceptable excipients in single or multiple doses.

The invention also relates to pharmaceutical compositions comprising a compound of formula (I) in combination with one or more, preferably one other active ingredient. The combinational composition comprises the compound of formula (I) together with one or more other active ingredients in a single dosage form together with pharmaceutically acceptable excipients. Other active ingredient is preferably a progestogenic compound, such as, but not limited to, progesterone, levonorgestrel, norgestimate, norethisterone, dydrogesterone, drospirenone, 3-beta-hydroxy-desogestrel, etonogestrel, 17-desacetyl-norgestimate, 19-norprogesterone, acetoxypregnenolone, allylestrenol, anagestone, chlormadinone, cyproterone, demegestone, desogestrel, dienogest, dihydrogesterone, dimethisterone, ethisterone, ethynodiol diacetate, flugestone acetate, gastrinone, gestodene, gestrinone, hydroxy-methylprogesterone, hydroxyprogesterone, lynestrenol, medrogestone, medroxyprogesterone, megestrol, melengestrol, nomegestrol, norethynodrel, norgestrel (including a d-norgestrel and d1-norgestrel), norgestrienone, normethisterone, quingestanol, (17alpha)-17-hydroxy-11-methylene-19-norpregna-4,15-diene-20-yn-3-one, tibolone, trimegestone, algestone acetophenide, nestorone, promegestone, 17-hydroxyprogesterone esters, 19-nor-17-hydroxyprogesterone, 17-alpha-ethynyl-testosterone, 17-alpha-ethynyl-19-nor-testosterone, d-17beta-acetoxy-13beta-ethyl-17-alpha-ethynyl-gon-4-en-3-one-oxim. More preferably, the progestogenic agent is drospirenone. Other active ingredient may also be calcium or vitamins, preferably e.g. and vitamin D.

The dosage required to achieve the desired therapeutic effect can vary within wide limits and will be adapted to the individual requirements in each case, taking into account the severity of the disease, the condition and weight of the patient to be treated, the sensitivity to the active ingredient, the route of administration and the number of daily treatments. Pharmaceutical compositions containing the active ingredient of formula (I) according to the invention generally comprise from 0.01 to 20 mg, preferably from 1.5 mg to 15 mg, more preferably 15 mg of active ingredient per dosage unit. When the composition also contains drospirenone as the other active ingredient, the composition will generally contain from 0.01 to 10 mg, preferably from 1.5 mg to 5 mg, more preferably 3 mg of drospirenone per dosage unit. The combination composition may also contain vitamin D.

The pharmaceutical compositions of the present invention may be prepared by methods known per se, for example by granulation (wet or dry) or by compression. The pharmaceutical compositions of the present invention may be formulated in a conventional manner using one or more physiologically (or pharmaceutically) acceptable excipients. Any technique and excipient well known in the art may be used, such excipients being selected from the following categories, such as, but not limited to, tablet excipients, tablet binders, release modifying agents, disintegrants, glidants, lubricants, sweeteners, flavoring agents, flavorings or coating materials. Examples of suitable pharmaceutical excipients are starch, microcrystalline cellulose, talc, glucose, lactose, gelatin, silica, magnesium stearate, sodium stearate, glycerol monostearate, cellulose derivatives, sodium chloride, glycerol, propylene glycol, water, ethanol and the like. The excipients described above and the various methods of preparation are only representative examples. Other materials and process techniques known in the art may also be used.

An embodiment of the invention is the use of estetrol of formula (I) obtained by the process described above for the manufacture of a medicament for hormone replacement therapy, a method of treating vaginal dryness, a method of treating perimenopausal symptoms (for example hot flashes, night sweats), a method of contraception, a method of enhancing libido, a method of treating skin and promoting wound healing, a method of treating or preventing an autoimmune disorder, breast tumors, prostate cancer and colorectal tumors, or for use in neuroprotection.

Another embodiment of the invention is preferably the use of estetrol of formula (I) obtained by the process described above for the manufacture of a medicament for use in contraception, more preferably in combination with drospirenone (WO 2019/154899 A1).

A further embodiment of the invention is preferably the use of estetrol of formula (I) obtained by the process described above for the manufacture of a medicament for use in hormone replacement therapy.

Another embodiment of the invention is preferably the use of estetrol of formula (I) obtained by the process described above for the manufacture of a medicament for use in neuroprotection (e.g. neonatal encephalopathy).

Another embodiment of the invention is the use of estetrol of formula (I) obtained by the process described above for the manufacture of a medicament for use in the treatment of perimenopausal symptoms, more preferably in combination with drospirenone and vitamin D.

Reference Example

Preparation of Estetrol Isomeric Mixture of ((15ξ, 16ξ,17β)-estra-1,3,5(10)-triene-3,15,16,17-tetrol) According to WO 2013/034780 A2 (Crystal Pharma)

a) Cis-hydroxylation (15α,16α,17β)-, and (15β,16β,17β)-3-(benzyloxy) estra-1,3,5(10)-triene-15,16,17-triol 20.0 g (55.5 mmol) 3-benzyloxy-estra-1,3,5(10),15-tetraene-17-ol (WO 2004/041839 (Pantarhei), Example 7) was dissolved in 1400 mL tetrahydrofuran at 20-25° C. under $N_2$ atmosphere, then a solution of 14 mL of 2 w/v % osmium tetroxide ($OsO_4$) in tert-butanol (280 mg $OsO_4$ content) and 11 g N-methylmorpholine N-oxide and 150 mL water were to the reaction mixture, and stirred for 24 hours under $N_2$ atmosphere at 20-25° C. The reaction was monitored by TLC (n-heptane:acetone 1:1).

Work-up: 140 ml of 5% $Na_2S_2O_5$ solution was added dropwise to the solution and 100 mg of activated carbon was added thereto, the mixture was stirred for 30 minutes, the mixture is filtered through a celite pad. The organic solvents were distilled off from the filtrate and 400 mL of dichloromethane was added. The phases were separated. The organic phase was washed with 200 mL of 10% hydrochloric acid, and with a solution of 200 mL of saturated sodium chloride, then dried, and concentrated. The concentrated residue was dissolved in 200 mL of methanol and added dropwise to 2 L of water at 0-5° C., stirred for 1 hour, filtered and the crystals were washed with 20 mL of water on the filter. The material was dried under vacuum at 40° C. to constant weight. 19.68 g (89.86%) of yellowish white crystals were obtained.

Purity (HPLC): 85.18% ααβ-isomer, 5.43% βββ-isomer (area) (ratio 94.0:6.0)

(15ξ,16ξ,17β)-estra-1,3,5(10)-triene-3,15,16,17-tetrol cemented (the crystals stick together, thus preventing the material from being filtered and recovered and thus from being purified) during recrystallizing in organic solvents, typically in hydrocarbons, ethers, esters, alcohols or mixtures thereof it. Typically, the compound can only be crystallized from water or a mixture of a water-miscible solvent (typically alcohols), but in this case no significant change can be achieved regarding the improvement of the isomer ratio.

b) Hydrogenation (15α,16α,17β)-, and (15β,16β,17β)-estra-1,3,5(10)-triene-15,16,17-triol 19.5 g of (15ξ,16ξ,17β)-3-(benzyloxy)estra-1,3,5(10)-triene-15,16,17-triol was dissolved in 400 mL of methanol at 20-25° C. under $N_2$ atmosphere. 2.0 g of 10% Pd/C catalyst was suspended in 100 mL of deep-frozen methanol, then added to the solution. The $N_2$ atmosphere was changed to $H_2$ atmosphere and the reaction mixture was stirred at 20-25° C. for 6 hours under atmospheric pressure.

Work-up: The catalyst was filtered off and the reaction mixture was concentrated to 45 mL under reduced pressure, 45 mL of water was added and the mixture was stirred at 0-5° C. for 1 hour, then filtered and washed twice with 20 mL of water on the filter, dried to constant weight, thus 14.5 g (96.67%) of white crystalline product was obtained.

Purity (HPLC): 87.53% ααβ-isomer, 5,46% βββ-isomer (area). (ratio 94.13:5.87)

The invention is further illustrated by the following non-limiting examples. From the above description and examples, one skilled in the art can ascertain the essential features of the invention and, without departing from the spirit and scope thereof, make certain changes and modifications in order to adapt the invention to various applications and circumstances. As a result, the invention is not limited to the illustrative examples described below, but rather to the scope of the appended claims.

EXAMPLES

Example 1

(15α,16α,17β)-3-(benzyloxy)estra-1,3,5(10)-triene-15,16,17-triyl triacetate

Method A (Isolated)

a.) Cis-hydroxylation (15α,16α,17β)-, and (15β,16β,17β)-3-(benzyloxy)estra-1,3,5(10)-triene-15,16,17-triol 40 mg potassium osmate dihydrate ($K_2OsO_4.2H_2O$) was suspended in 100 mL of 2-butanone (methyl ethyl ketone) at 20-25° C. under $N_2$ atmosphere and 7.7 mL of purified water and 1.1 g of trimethyl-amine N-oxide dihydrate was added thereto. 2.0 g (5.5 mmol) of 3-benzyloxy-estra-1,3,5(10),15-tetraene-17-ol (WO 2004/041839 (Pantarhei), Example 7) was dissolved in 40 mL of 2-butanon and added dropwise to the reaction mixture. The reaction mixture was then stirred at 20-25° C. for 28 hours under $N_2$ atmosphere. The reaction was monitored by TPLC (n-heptane:acetone 1:1).

Work-up: 25 mL of 10% $Na_2S_2O_5$ solution was added to the mixture followed by the addition of 100 mg of activated carbon, then stirred for 1 hour. Filtered through a celite pad, then EtOAc and 10% of HCl solution were added. The phases were separated, the aqueous phase was extracted with EtOAc. The combined organic phases was washed with saturated NaCl and 10% $Na_2S_2O_5$ solutions. Dried over $Na_2SO_4$, filtered, then concentrated. Thus, 1.8 g (81.8%) of product was obtained.

Purity (HPLC): 85.0% ααβ-isomer, 9.9% βββ-isomer (area) (ratio 89.6:10.4)

b) Acylation (15α,16α,17β)-3-(benzyloxy)estra-1,3,5(10)-triene-15,16,17-triol triacetate 1.0 g (2.53 mmol) of (15α,16α,17β)-3-(benzyloxy)estra-1,3,5(10)-triene-15,16,17-triol was dissolved in 15 mL of dichloromethane under $N_2$ atmosphere. 1.5 mL of triethylamine, 6.0 mL of acetic acid and 72 mg of 4-dimethyllaminopyridin were added and stirred for 2 hours. The reaction was monitored by TLC (toluene:acetone 4:1).

Work-up: 3 mL of ethanol was added dropwise to the mixture an stirred for 30 minutes, then 10% $NaHCO_3$ solution was added and stirred for another 30 minutes. The phases were separated and the organic phase was washed twice with 10% $NaHCO_3$ solution, then with saturated brine. Dried over $Na_2SO_4$, filtered and the solvent was changed to MeOH and crystallized therefrom. After filtration and drying 1.2 g of material was obtained. To obtain the appropriate isomer ratio the product was recrystallized twice more from methanol, thus 1.1 g (84.46%) of product was obtained.

Purity (HPLC): 99.2% ααβ-isomer, 0.14% βββ-isomer (area).

Method B (without Isolation)

a) Cis-Hydroxylation (15α,16α,17β), (15β,16β,17β) Isomeric Mixture of 3-(benzyloxy)estra-1,3,5(10)-triene-15,16,17-triol 30.03 g (83.3 mmol) of 3-benzyloxy-estra-1,3,5(10),15-tetraene-17-ol (WO 2004/041839 (Pantarhei), Example 7) was dissolved in 480 mL of 2-butanon (methyl ethyl ketone) at 20-25° C. under $N_2$ atmosphere, then 600 mg of potassium osmate dihydrate ($K_2OsO_4.2H_2O$), 48.0 mL of purified water and 16.5 g of trimethylamine N-oxide dihydrate were added. The reaction mixture was then stirred at 40-45° C. for 7 hours under $N_2$ atmosphere. The reaction was monitored by TLC (n-heptane:acetone 1:1).

Work-up: 300 mL of 10% (w/v) sodium metabisulfite solution (sodium pyrosulfite) was added dropwise to the mixture at 40-45° C. and stirred for 1 hour. The slurry was then filtered through a celite pad and the filter was washed with 2-butanone. The 2-butanone was then removed from the filtrate by distillation. 600.0 mL of ethyl acetate and 300 mL of 10% (w/v) sodium hydrogen carbonate solution (30 g $NaHCO_3$) was added to the residue, after stirring vigorously for a few minutes and then settling, the phases were separated. The aqueous phase was washed twice with ethyl acetate. The combined organic phase was washed with a mixture of 1% (w/v) EDTA-tetraNa salt solution and saturated brine. After separation of the phases, the ethyl acetate organic phase was concentrated to a final volume of 450 mL, thereby dehydrated also. The product was not isolated but further transferred to an acylation reaction.

b) Acylation (15α,16α,17β)-3-(benzyloxy)estra-1,3,5(10)-triene-15,16,17-triyl triacetate 72.0 mL of acetic anhydride, 48 mL of triethylamine and 1.8 g of 4-dimethylaminopyridine were added to the ethyl acetate solution obtained in step a), followed by stirring at 35-40° C. for 3 hours under $N_2$ atmosphere. The reaction was monitored by TLC (toluene:acetone 4:1).

Work-up: 24 mL of ethanol was added dropwise to the mixture, stirred for 30 minutes, then cooled to 20-25° C., followed by the addition of 240 mL of purified water and 60 mL of 10% (w/v, d=1.047, 17.88 g cc.HCl) hydrochloric acid solution and after a few minutes of vigorous stirring and then settling, the phases were separated. The aqueous phase was extracted with ethyl acetate. The combined organic phase was washed with a mixture of 10% (w/v) sodium hydrogen carbonate solution and saturated brine, and the phases were separated. The organic phase was dried over $Na_2SO_4$, clarified with alumina, silica gel and activated carbon and stirred at 20-25° C. for 1 hour. The clarifiers were then filtered off and the filter was washed with ethyl acetate.

The filtrate was concentrated under reduced pressure, then the solvent was concentrated and distilled to change the solvent to methanol, and finally the material was crystallized from pure methanol. The obtained crude product was recrystallized without drying.

c) Recrystallization

The crude product obtained in step b) was dissolved in dichloromethane, methanol was distilled off and finally crystallized from pure methanol. The operation was repeated once more. Thus, 30.4 g (69.8%) of white crystals was obtained.

Purity (HPLC): 99.2% ααβ-isomer, 0.14% βββ-isomer (area).

Mp.: 156.5-157.5° C.

EI-HRMS: Calcd for $C_{31}H_{36}O_7$ [M$^+$]: 520.24555; found: 520.24459; delta=−1.86 ppm.

$^1$H NMR (499.9 MHz, CDCl$_3$) δ=5.39 (1H, dd, J=8.4 Hz, J=6.6 Hz, H-16), 5.16 (1H, dd, J=10.4 Hz, J=8.4 Hz, H-15), 5.01 (1H, d, J=6.6 Hz, H-17), 2.08 (3H, s, 17-acetyl), 2.06 (3H, s, 15-acetyl), 2.04 (3H, s, 16-acetyl), 0.94 (3H, s, H-18)

$^{13}$C NMR (125.7 MHz, CDCl$_3$) δ=169.8 (17-acetyl CO C-20), 169.0 (15-acetyl CO), 168.7 (16-acetyl CO), 83.1 (C-17), 72.5 (C-16), 69.8 (C-15), 51.4 (C-14), 39.2 (C-13), 19.9 (17-acetyl-CH$_3$), 19.7 (15-acetyl-CH$_3$), 19.6 (16-acetyl-CH$_3$), 13.5 (C-18)

Example 2

(15α,16α,17β)-3-hydroxyestra-1,3,5(10)-triene-15,16,17-triyl triacetate

Method A 25.7 g (49.36 mmol) of (15α,16α,17β)-3-(benzyloxy)estra-1,3,5(10)-triene-15,16,17-triyl triacetate (Example 1) was dissolved in 315 mL of ethyl acetate at 20-25° C. under N$_2$ atmosphere. 770 mg of 10% palladium-on-carbon catalyst was suspended in 19 mL of deep-frozen ethyl acetate, and then added to the solution. The N$_2$ atmosphere was changed to H$_2$ atmosphere and the reaction mixture was stirred at 20-25° C. for 3 hours under atmospheric pressure.

Work-up: The catalyst was filtered off, washed with ethyl acetate and concentrated to a final volume under reduced pressure, then n-heptane was added and the suspension was kept at 0-5° C. for 1 hour, then filtered and the crystalline product was washed on the filter with n-heptane, and dried at 40° C. in vacuum to constant weight. Thus, 19.88 g (93.55%) of white crystalline product was obtained.

Purity (HPLC): 99.42% ααβ-isomer, 0.04% βββ-isomer (area).

Method B 0.5 g of (15α,16α,17β)-3-(benzyloxy)estra-1,3,5(10)-triene-15,16,17-triyl triacetate (Example 1) was suspended in 14 mL of ethanol at 20-25° C., then 0.5 mL of cyclohexene and 38 mg of 10% Pd/C catalyst was added, followed by stirring at reflux temperature for 1 hour. The reaction was monitored by TLC (toluene:acetone 4:1).

Work-up: The catalyst was filtered off from the reaction mixture and the mixture was concentrated to dryness. Thus, 0.41 g (99.17%) of white crystalline product was obtained.

Purity (HPLC): 97.99% ααβ-isomer, 0.14% βββ-isomer (area).

Mp.: 181.5-185.5° C.

EI-HRMS: Calcd for $C_{24}H_{30}O_7$ [M$^+$]: 430.19860; found: 430.19927; delta=1.55 ppm.

$^1$H NMR (499.9 MHz, CDCl$_3$) δ=5.41 (1H, dd, J=8.4 Hz, J=6.6 Hz, H-16), 5.18 (1H, dd, J=10.5 Hz, J=8.4 Hz, H-15), 5.03 (1H, d, J=6.6 Hz, H-17), (3H, s, 17-acetyl), 2.10 (3H, s, 15-acetyl), 2.07 (3H, s, 16-acetyl), 1.77 (1H, t, J=11.1 Hz, H-14), 0.95 (3H, s, H-18)

$^{13}$C NMR (125.7 MHz, CDCl$_3$) δ=170.9 (17-acetyl CO), 170.1 (15-acetyl CO), 169.8 (16-acetyl CO), 84.1 (C-17), 73.5 (C-16), 70.8 (C-15), 52.4 (C-14), 40.2 (C-13), 20.9 (17-acetyl-CH$_3$), 20.7 (15-acetyl-CH$_3$), 20.6 (16-acetyl-CH$_3$), 14.5 (C-18)

Example 3

(15α,16α,17β)-3-(benzyloxy)estra-1,3,5(10)-triene-15,16,17-triyl triformiate 5.00 g of (15α,16α,17β)-3-(benzyloxy)estra-1,3,5(10)-triene-15,16,17-triol (Example 1, Method "A", step a)) was dissolved in 73 mL of pyridine, and cooled to 0° C., then a mixture of a mixed anhydride made of 49 mL of formic acid and 18.3 mL of acetic anhydride cooled to 0° C. was added via an addition funnel at between 0-10° C. in ca. 25 minutes. After stirring for 1 hour 305 mL of water was added to the reaction mixture, and the resulting white precipitate was filtered off and washed with water. The dry crude product weighted 5.65 g (93.23%).

The crude product—according to Example 1 Method B step c)—was recrystallized from methanol to give 3.92 g (69.4%) of the pure title product as white crystal.

Purity (HPLC): 99.2% ααβ-isomer, 0.05% βββ-isomer (area).

Mp.: 153.5-154.3° C.

EI HRMS: M=478.19866; delta=0.06 ppm; $C_{28}H_{30}O_7$ $^1$H NMR (499.9 MHz, CDCl$_3$) δ=5.41 (1H, dd, J=8.4 Hz, J=6.6 Hz, H-16), 5.18 (1H, dd, J=10.5 Hz, J=8.4 Hz, H-15), 5.03 (1H, d, J=6.6 Hz, H-17), (3H, s, 17-acetyl), 2.10 (3H, s, 15-acetyl), 2.07 (3H, s, 16-acetyl), 1.77 (1H, t, J=11.1 Hz, H-14), 0.95 (3H, s, H-18)

$^{13}$C NMR (125.7 MHz, CDCl$_3$) δ=170.9 (17-acetyl CO), 170.1 (15-acetyl CO), 169.8 (16-acetyl CO), 84.1 (C-17), 73.5 (C-16), 70.8 (C-15), 52.4 (C-14), 40.2 (C-13), 20.9 (17-acetyl-CH$_3$), 20.7 (15-acetyl-CH$_3$), 20.6 (16-acetyl-CH$_3$), 14.5 (C-18)

Example 4

(15α,16α,17β)-3-hydroxyestra-1,3,5(10)-triene-15,16,17-triyl triformiate 5.0 g of (15α,16α,17β)-3-(benzyloxy)estra-1,3,5(10)-triene-15,16,17-triyl triformiate (Example 3) was dissolved in 150 mL of ethyl acetate at 20-25° C. under N$_2$ atmosphere. 380 mg of 10% Pd/C catalyst was suspended in 5 mL of deep-frozen ethyl acetate and added to the solution. The N$_2$ atmosphere was changed to H$_2$ atmosphere and the reaction mixture was stirred at 20-25° C. for 4 hours under atmospheric pressure.

Work-up: The catalyst was filtered off and the reaction mixture was concentrated to a quarter (38 mL) under reduced pressure, then 52 mL of n-heptane was added. After stirring at 0-5° C. for 1 hour, it was filtered and washed on the filter twice with 16 mL of n-heptane, dried to constant weight, thus, 3.51 g (94%) of white crystalline product was obtained.

Purity (HPLC): 99.42% ααβ-isomer, 0.04% βββ-isomer (area).

Mp.: 234-235° C.

MS: M-H=387 (ESI)

$^1$H NMR (499.9 MHz, DMSO-d$_6$) δ=8.17 (1H, s, 17-formyl-H), 8.09 (1H, s, 15-formyl-H), 8.04 (1H, s, 16-formyl-H), 5.52 (1H, t, J=7.4 Hz, H-16), 5.24 (1H, dd, J=10.1 Hz, J=8.6 Hz, H-15), 5.11 (1H, d, J=6.5 Hz, H-17), 0.99 (3H, s, H-18)

$^{13}$C NMR (125.7 MHz, DMSO-d$_6$) δ=159.5 (17-formyl-C), 159.3 (15-formyl-C), 158.8 (16-formyl-C), 82.4 (C-17), 71.7 (C-16), 69.2 (C-15), 51.3 (C-14), 39.6 (C-13), 13.5 (C-18)

Example 5

Estetrol ((15α,16α,17β)-estra-1,3,5(10)-triene-3,15,16,17-tetrol)

Method A 19.88 g (46.18 mmol) of (15α,16α,17β)-3-hydroxyestra-1,3,5(10)-triene-15,16,17-triyl triacetate (Example 2) was suspended in 596 mL of methanol at 20-25° C. under N$_2$ atmosphere, then 19.88 g potassium carbonate was added portionwise and stirred for 3 hours. The reaction was monitored by TLC (n-heptane:acetone 1:1).

Work-up: 14.91 mL of cc. acetic acid was added to the mixture and stirred for 30 minutes, after adding 298 mL of water the methanol was removed by distillation, then the precipitated crystals were kept at 0-5° C. for 1 hour, filtered and washed with water on the filter. It was then dried at 40° C. under vacuum to constant weight. Thus, 13.66 g (97.22%) of white crystalline product was obtained.

Purity (HPLC): 99.67% ααβ-isomer, 0.04% βββ isomer (area), all contaminants <0.10%

Method B 5 g (12.87 mmol) of (15α,16α,17β)-3-hydroxyestra-1,3,5(10)-triene-15,16,17-triyl triformiate (Example 4) was suspended in 150 mL of methanol at 20-25° C. under N$_2$ atmosphere, then 5.34 g (38.6 mmol) of potassium carbonate was added portionwise and stirred for 3 hours. The reaction was monitored by TLC (n-heptane:acetone 1:1).

Work-up: 4 mL of acetic acid was added to the mixture and stirred for 30 minutes, after adding 75 mL of water the methanol was removed from the mixture by distillation, the precipitated crystals were kept at 0-5° C. for 1 hour, then filtered and washed on the filter twice with 5 mL of 0-5° C. water. It was then dried at 40° C. under vacuum to constant weight. Thus, 3.80 g (97%) of white crystalline product was obtained.

Purity (HPLC): 99.67% ααβ-isomer, 0.04% βββ isomer (area), all contaminants <0.10%

Mp.: 240-243° C.

EI-HRMS: Calcd for C$_{18}$H$_{24}$O$_4$[M$^+$]: 304.16691; found: 304.16716; delta=0.82 ppm.

$^1$H NMR (499.9 MHz, DMSO-d$_6$) δ=4.86 (1H, d, J=4.8 Hz, OH (17)), 4.61 (1H, br s, OH (16)), 4.26 (1H, br d, J=3.3 Hz, OH (15)), 3.55-3.78 (2H, m, H-16, 15), 3.25 (1H, dd, J=5.7, 4.7 Hz, H-17), 1.05 (1H, dd, J=10.9 Hz, J=9.4 Hz, H-14), 0.67 (3H, s, H-18)

$^{13}$C NMR (125.7 MHz, DMSO-d$_6$) δ=86.3 (C-17), 75.0 (C-16), 69.2 (C-15), 55.5 (C-14), 39.5 (C-13), 14.0 (C-18)

The invention claimed is:

1. Process for the preparation of estetrol of formula (I),

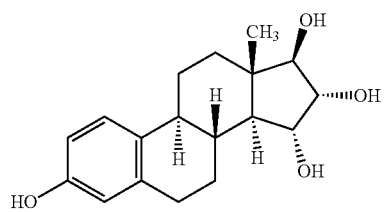

starting from the compound of formula (II)

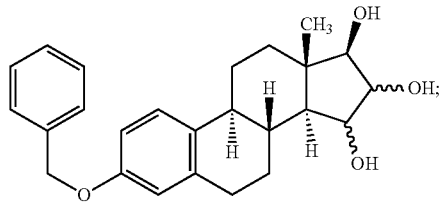

wherein the process comprises:

(a) acylating a compound of formula (II) in a suitable solvent using a suitable reactant to give a compound of general formula (III);

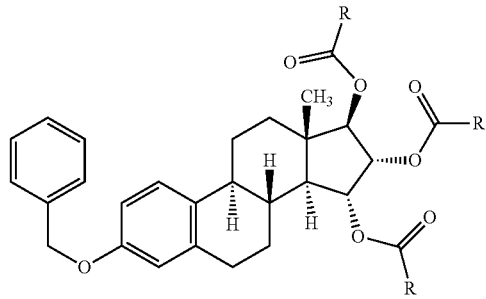

wherein R=methyl group or hydrogen;

(b) of removing a benzyl protecting group in position 3 by transfer hydrogenation or catalytic hydrogenation to give a compound of general formula (IV)

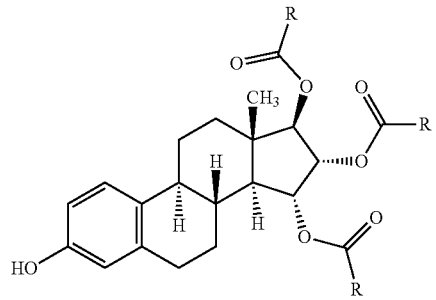

wherein R=methyl group or hydrogen; and (c) deprotecting the compound of formula (IV) in an alkaline medium with an alkali metal carbonate, alkali metal hydrogen carbonate, or alkali metal hydroxides in a suitable solvent.

2. The process according to claim 1, wherein the solvent used in step (a) is selected from the group consisting of aliphatic and aromatic hydrocarbons, halogenated hydrocarbons, esters, and ethers.

3. The process according to claim 1, wherein the reactant used in step (a) is acetic anhydride, acetyl chloride, acetyl bromide, or acetic acid-formic acid mixed anhydride.

4. The process according to claim 1, wherein step (a) is carried out in the presence of a tertiary amine base.

5. The process according to claim 1, wherein step (a) further comprises crystallizing the resulting compound of general formula (III) from $C_{1-3}$ alcohols.

6. The process according to claim 1, wherein step (a) is carried out without the purification and/or isolation of the compounds of formula (II).

7. The process according to claim 1, wherein step (b) is carried out by catalytic hydrogenation with hydrogen gas, wherein the catalyst is selected from palladium or palladium on a support.

8. The process according to claim 7, wherein the catalytic hydrogenation uses a solvent selected from the group consisting of alcohols, esters, and ketones.

9. The process according to claim 1, wherein step (b) is carried out by transfer hydrogenation using a cyclohexene reagent.

10. The process according to claim 9, wherein the transfer hydrogenation uses an alcohol solvent.

11. The process according to claim 1, wherein step (b) further comprises crystallizing the resulting compound of general formula (IV) from esters, hydrocarbons, alcohols, or mixtures thereof.

12. The process according to claim 1, wherein the solvent used in step (c) is selected from the group consisting of water, an alcoholic solvent, or a mixture thereof.

13. The process according to claim 1, wherein the step (c) is carried out in the presence of an alkali metal carbonate, an alkali metal hydrogen carbonate, an alkali metal alcoholate, or an alkali metal hydroxide.

14. The process according to claim 1, wherein R is a methyl group.

15. The process according to claim 1, wherein R is hydrogen.

16. A compound selected from the group consisting of (15α,16α,17β)-3-(benzyloxy)estra-1,3,5(10)-triene-15,16,17-triyltriacetate, (15α,16α,17β)-3-(benzyloxy)estra-1,3,5(10)-triene-15,16,17-triyl triformiate, and (15α,16α,17β)-3-hydroxyestra-1,3,5(10)-triene-15,16,17-triyl triformiate.

* * * * *

UNITED STATES PATENT AND TRADEMARK OFFICE
CERTIFICATE OF CORRECTION

PATENT NO. : 11,633,406 B2
APPLICATION NO. : 17/639206
DATED : April 25, 2023
INVENTOR(S) : Lovas et al.

It is certified that error appears in the above-identified patent and that said Letters Patent is hereby corrected as shown below:

In the Specification

In Column 1, Line 43, delete "encephalophaty)" and insert -- encephalopathy) --, therefor.

In Column 11, Line 9, delete "triformiate" and insert -- triformate --, therefor.

In Column 11, Line 38, delete "triformiate" and insert -- triformate --, therefor.

In Column 12, Line 48, delete "gastrinone," and insert -- gestrinone, --, therefor.

In Column 12, Line 54, delete "normethisterone," and insert -- norethisterone, --, therefor.

In Column 15, Line 1, delete "BBB" and insert -- βββ --, therefor.

In Column 18, Line 8, delete "triformiate" and insert -- triformate --, therefor.

In Column 18, Line 42, delete "triformiate" and insert -- triformate --, therefor.

In Column 18, Line 45, delete "triformiate" and insert -- triformate --, therefor.

In Column 19, Line 28, delete "triformiate" and insert -- triformate --, therefor.

In the Claims

In Column 19, Claim 1, Line 55, delete "Process" and insert -- A process --, therefor.

In Column 20, Claim 1, Line 36, delete "of" before "removing".

Signed and Sealed this
Twenty-seventh Day of June, 2023

Katherine Kelly Vidal
*Director of the United States Patent and Trademark Office*

In Column 22, Claim 16, Line 19, delete "triformiate," and insert -- triformate, --, therefor.

In Column 22, Claim 16, Line 20, delete "triformiate." and insert -- triformate. --, therefor.